United States Patent [19]

Möhring et al.

[11] Patent Number: 5,403,296
[45] Date of Patent: Apr. 4, 1995

[54] PUNCTURING INSTRUMENT

[76] Inventors: Klaus Möhring, Uferstrasse 40, D-6900 Heidelberg; Josef Magasi, Wendelinusstrasse 8, D-6902 Sandhausen, both of Germany

[21] Appl. No.: 166,654

[22] Filed: Dec. 13, 1993

Related U.S. Application Data

[63] Continuation of Ser. No. 777,221, filed as PCT/DE90/00328, May 7, 1990, published as WO 90/13330, Nov. 15, 1990, abandoned.

[30] Foreign Application Priority Data

May 5, 1989 [DE] Germany .................. 39 15 215.4

[51] Int. Cl.⁶ .............................................. A61M 5/32
[52] U.S. Cl. ........................................ 604/274; 604/158
[58] Field of Search ............. 604/158, 161, 164, 165, 604/170, 274

[56] References Cited

U.S. PATENT DOCUMENTS

| | | | |
|---|---|---|---|
| 2,630,803 | 3/1953 | Baran | 604/158 |
| 2,717,599 | 9/1955 | Huber | 128/221 |
| 2,922,420 | 1/1960 | Cheng | 604/158 |
| 3,399,674 | 3/1988 | Pannier et al. | 128/214.4 |
| 3,677,243 | 7/1972 | Nerz | 128/214.4 |
| 4,354,491 | 10/1982 | Marbry | 604/161 |
| 4,451,256 | 5/1984 | Weikl et al. | 604/164 |
| 4,518,383 | 5/1985 | Evans | 604/272 |
| 4,596,559 | 6/1986 | Fleischhacker | 604/161 |
| 4,753,641 | 6/1988 | Vaslow | 604/279 |
| 4,846,799 | 7/1989 | Tanaka et al. | 604/158 |
| 4,889,529 | 12/1989 | Handl | 604/274 |
| 4,911,691 | 3/1990 | Aniuk et al. | 604/158 |
| 4,983,168 | 1/1991 | Moorehead | 604/161 |
| 5,106,376 | 4/1992 | Mononen et al. | 604/158 |

FOREIGN PATENT DOCUMENTS

| | | | |
|---|---|---|---|
| 0064212 | 11/1982 | European Pat. Off. | A61M 25/00 |
| 3048774 | 3/1984 | Germany | A61M 5/14 |
| 3218242 | 1/1987 | Germany | A61M 5/32 |
| 3643235 | 11/1987 | Germany | A61M 19/00 |
| 3712869 | 11/1988 | Germany | A61B 17/34 |

OTHER PUBLICATIONS

Dow Corning "Silastic Cystocath" May 1976 8 pages.

*Primary Examiner*—Paul J. Hirsch
*Attorney, Agent, or Firm*—Christie, Parker & Hale

[57] ABSTRACT

The invention relates to a puncturing instrument which comprises a puncturing tube and a conforming puncture instrument. A channel-like prick incision lance 5 projecting out of the puncturing tube 2 serves as the puncture instrument. The puncturing tube 2 has at the lower end a pipe bend section 14 which forms a displacement section in the form of a ship's bow. Through this design the puncturing instrument 1 receives a puncturing end which has the action of a puncturing point or puncturing needle. Punching out of the tissue during puncturing is prevented and the manipulation resistance is reduced.

20 Claims, 3 Drawing Sheets

PUNCTURING INSTRUMENT

This application is a continuation of U.S. patent application. Ser. No. 07/777,221, filed as PCT/DE90/00328, May 7, 1990, published as WO 90/13330, Nov. 15, 1990, now abandoned.

The invention relates to a device according to the preamble of patent claim 1.

A two-part catheterising device is known from DE C 30 48 774 wherein the puncturing tube has a handle. Before puncturing, a tubular steel hypodermic syringe is inserted into this puncturing tube, the syringe having an inclined cutting edge at its front end and a handle at its rear end. With this known catheterizing device there are two axially spaced handles. When piercing through the skin this known catheterizing device acts like the annular end edge of a cylindrical punch. Despite the inclined cutting edge when the catheterizing device is pressed into the skin or into the body tissue the known device punches out wads of skin and tissue from the body part which are pressed into the hollow cavity of the syringe. Pressing the circular ring shaped end edges of this device into human or animal tissue, particularly into muscle tissue is opposed by a high resistance which must be overcome by corresponding forces. The circular ring shaped punching edge thereby considerably increases the risk of injuring vessels. Transport of the punched-out skin and tissue parts into other regions of the body takes place automatically and this transport can have undesired consequences, such as for example infections. With these known devices, in the case of suprapubic urine removal it can result in a not inconsiderable traumatizing of the filled bladder wall, also partly in the punching out of the tissue surrounding the bladder and in considerable hemorrhaging around the bladder or in the bladder lumen.

In the leaflet 51-240-03, May 1976 of Messrs. DOW CORNING EUROPE, Brussels there is a description of a suprapubic drainage system by Reif which has a trocar with a pyramid shaped point in a cylindrical cannula. When inserting this instrument a high resistance has to be overcome since its point penetrates bluntly into the skin and drives out the tissue.

The object of the invention is to produce a puncturing instrument whereby during puncturing the punching out of body or organ parts is substantially avoided.

This is achieved according to the invention through the technical teaching of patent claim 1.

Advantageously the puncturing instrument which can be fitted into the puncturing tube is a partially cylindrically curved channelled prick incision lance. This channelled prick incision lance is not a fully cylindrical component and has no circular ring shaped end wall which punches out wad-like body parts. Advantageously the cutting edge of the prick incision lance is designed so that the closest possible straight line cut can be achieved. A section of a pipe bend is formed in a special way at the end of the puncturing tube. The outer radius, or outer radius curved end, curved end of this pipe bend section extends up to the channelled inside of the inserted prick incision lance and adjoins same. The opening edge of this pipe bend section thereby extends over the channelled side edges of the prick incision lance into the channelled inside. This opening edge forms a spatial curve which is curved into two directions at right angles to each other and consists of two curved sections which are mirror symmetrical relative to the dividing plane of the puncturing tube. Through this design the lower end of the puncturing tube is not an open and thus punching ring, as in the case of known instruments, but forms a sealing end which adjoins the prick incision lance in the form of a ship's bow. This ship's bow like sealing end which directly adjoins the prick incisions lance, displaces the tissue as the instrument is inserted into the body and itself, exerts hardly any cutting action. Punching is substantially eliminated; the tissue parts cut by the prick incision lance are only displaced. In addition to avoiding undesired punching or cutting actions the intrusion resistance is considerably reduced. The design of the instrument point is optimally like that of a sharp needle or point.

The design of the puncturing instrument according to the invention also has the advantage that ultrasonically controlled puncturing is made easier. The points of the known puncturing instruments are not very echogenic, i.e. they do not produce sufficient image to control the puncturing by means of ultrasound. With the subject of the invention the echo patterns are good, even excellent in part.

The partially cylindrically curved channelled design of the prick incision lance allows the cutting edge to be designed lancet sharp with the desired angle.

An ergonomic optimum design of the instrument is achieved in that the handle of the prick incision lance has an underside which is complementary with the upper side of the puncturing tube, and also has two detent pins and a socket groove. Through this design the handle parts can be combined into one integral handle. The elongated object which is to be inserted, such as a catheter, is placed in the socket groove. This elongated object is prevented from moving axially out of the instrument so that handling the instrument is much easier. Furthermore to improve handling, the handle of the prick incision lance is provided on the top side with channels, particularly in the area where the thumb can be placed.

In a particularly advantageous design of the puncturing instrument according to the invention, the puncturing tube can be divided and can therefore for example be drawn out of the body after placing the catheter and can then be removed by simply drawing apart the two parts.

Each half of the divisible puncturing tube can support a complementary section of a handle fitted with a detent groove. Through this design the two tube sections of the divisible puncturing tube can be locked together.

An embodiment of the invention will now be explained with reference to the figures in the drawing in which.

Figure 1:
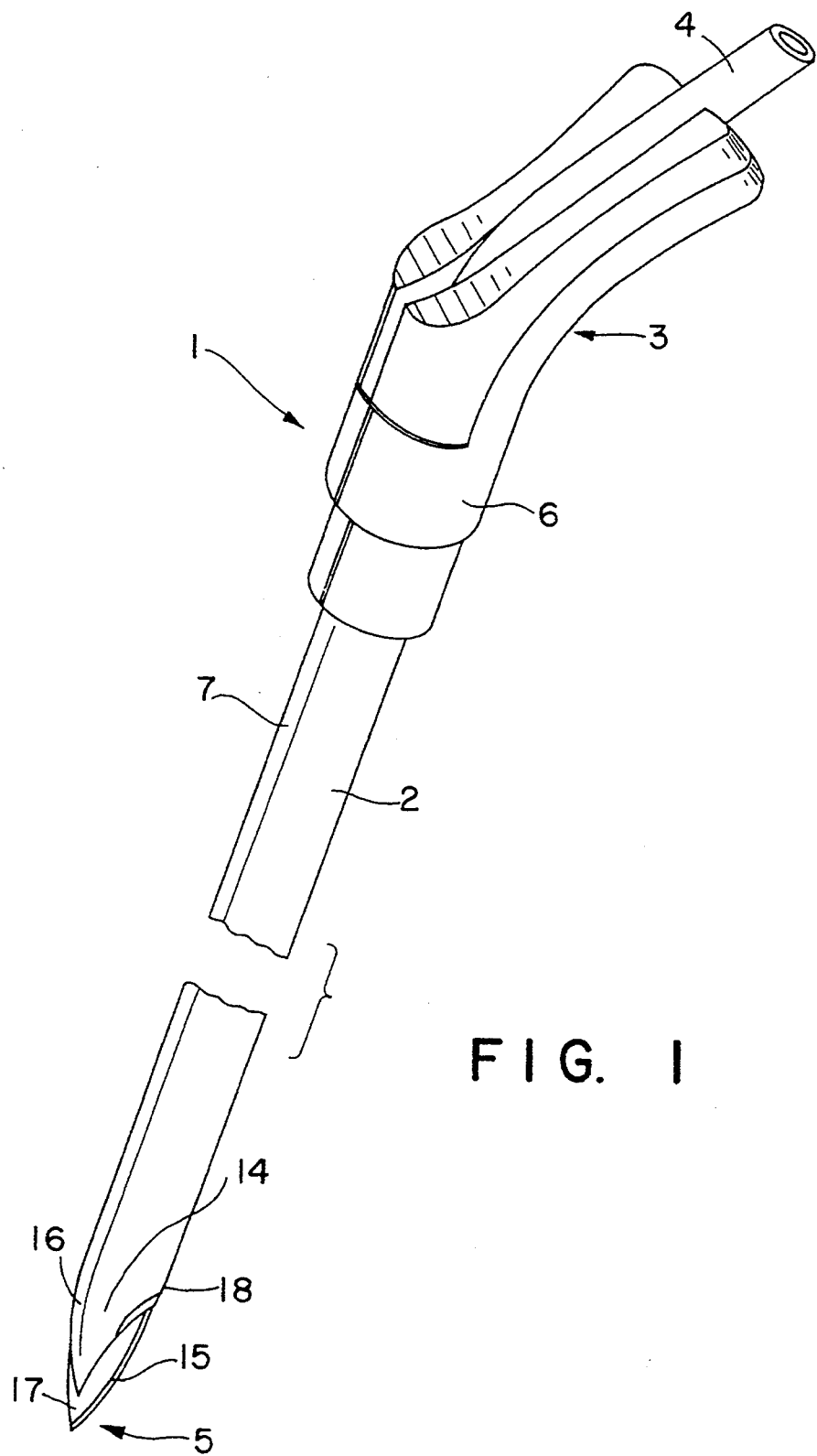
FIG. 1 is a diagrammatic perspective view of a puncturing instrument.

The puncturing instrument 1 shown in FIG. 1 has a divided puncturing tube 2. The abutting edges of the assembled puncturing tube 2 are shown at 7. The dividing plane of the puncturing tube 2 extends through these edges 7.

Figure 2:
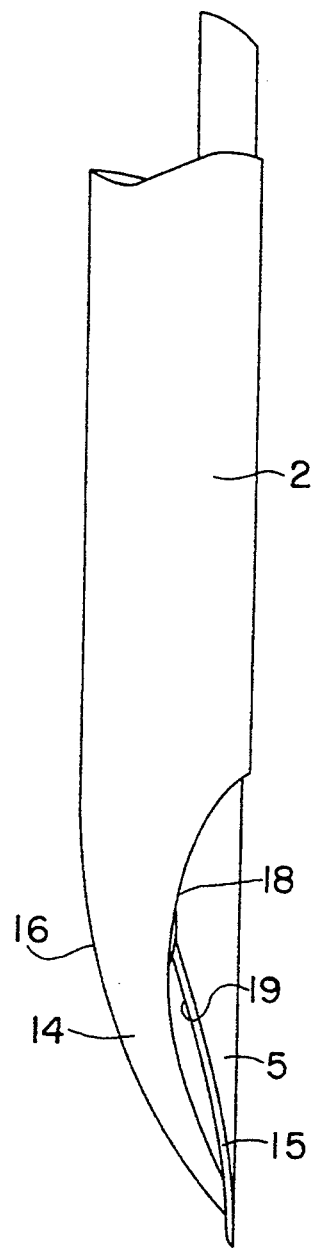
FIG. 2 is an enlarged detailed view of the lower end of the puncturing instrument.
Figure 3:
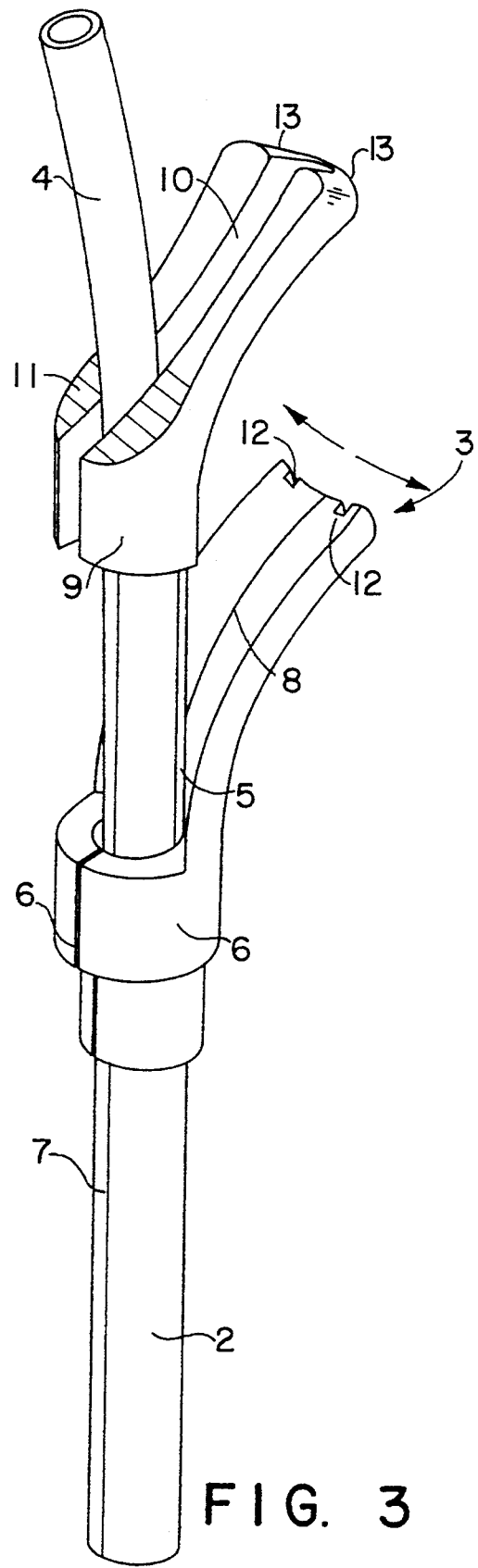
FIGS. 3 and 4 are perspective views of the upper end of the puncturing instrument in two different operating positions.
Figure 4:
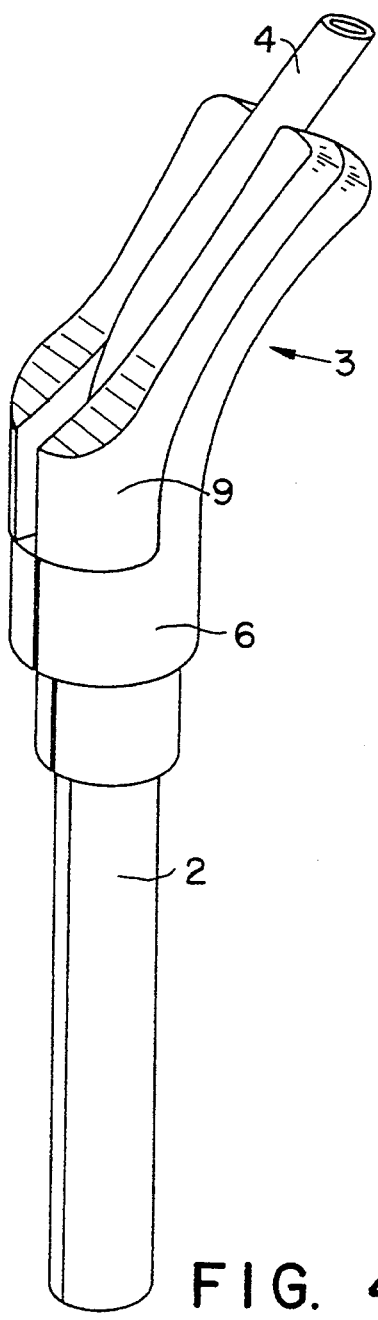

As shown in FIG. 3, a partially cylindrically curved channel-like prick incision lance 5 is inserted in this puncturing tube 2. The outer circumference of this channel like prick incision lance 5 conforms with the inner circumference of the puncturing tube 2. In the inserted state which is shown in FIGS. 1, 2 and 4, the lower end of the prick incision lance 5 extends out of the puncturing tube 2, as shown in FIGS. 1 and 2. At the lower end of the prick incision lance there is a pointed lancet tip 15.

As shown in FIGS. 1 and 2 at the lower end of the divided tube 2 there is a section 14 of a pipe bend. The pipe bend is trimmed by cross cutting, as shown. By cutting, an opening edge 18 is produced which forms a spatial curve which is bent in two directions at right angles to each other. As can be seen from FIG. 2, this opening edge 18 starts at the top at a position lying in the area of the abutting edges 7 of the divided puncturing tube 2. The opening edge 18 is designed so that the outer radius arc 16 shown in FIGS. 1 and 2 extends up to the channel inside 17 and adjoins same. The opening edge 18 extends over both channel side edges 19 towards the channel inside 17 so that as shown in FIG. 1 the lower edge of the puncturing tube 2 has the shape of a wedged or tapered displacement body whose point adjoins the channel inside 17 of the partially cylindrically curved, channelled prick incision lance 5.

As shown in FIGS. 3 and 4 each half of the puncturing tube 2 has a complementary section 6 of a handle 3. The butt edge in the installed state is marked 8 in FIG. 3. These complementary sections 6 are provided on the outside edge with detent grooves 12.

At the end of the prick incision lance 5 there is a handle 9 which has a socket groove 10 and detent grooves 13 at the end. In the assembled state which is shown in FIG. 4, the detent noses 13 engage in the detent grooves 12 of the complementary sections 6 of the handle 3 and thus lock the components.

FIGS. 1, 3 and 4 diagrammatically show a catheter 4 which is to be introduced into the body with the puncturing instrument 1. As shown in FIG. 4, the catheter 4 can be placed into the socket groove 10 (FIG. 3) of the handle 9. When the hand of the user grasps the handle which as shown in FIG. 4 comprises the grip parts 3 and 9 the, manipulation is not destroyed by an axially extending catheter 4. Fluting 11 on the top side of the handle 3 makes manipulation easier.

We claim:

1. A medical puncturing instrument, comprising a puncturing tube and a conforming puncture instrument, characterized in that: the puncture instrument is a partially cylindrically curved channel-like prick incision lance; the channel-like prick incision lance defines a channel, the channel having an inner surface; the puncturing tube has a handle; the puncturing tube is designed, at the end, as a section of a pipe bend having an outer radius curve; and the outer radius curve end of the section of pipe bend makes contact with the channel inner surface of the inserted prick incision lance.

2. The medical puncturing instrument according to claim 1, wherein:
   said puncturing tube comprises a major portion having a cylindrical shape;
   said major portion of said puncturing tube has an inner cylindrical surface;
   said inner cylindrical surface of said major portion of said puncturing tube has a circumference;
   said prick incision lance conforms to said inner cylindrical surface of said major portion of said puncturing tube;
   said prick incision lance is disposed about a limited portion of the circumference of said inner cylindrical surface of said puncturing tube;
   said puncturing tube defining a central longitudinal axis, the central longitudinal axis being centrally disposed with respect to said major portion of said puncturing tube;
   said section of pipe bend of said first end portion of said puncturing tube is bent inwardly, towards the central longitudinal axis of said puncturing tube;
   said major portion of said puncturing tube is substantially straight with respect to the longitudinal axis of said puncturing tube;
   said prick incision lance comprises an end portion disposed adjacent said end of said puncturing tube; and
   said end portion of said prick incision lance is substantially straight with respect to the longitudinal axis of said puncturing tube.

3. The medical puncturing instrument according to claim 2, characterized in that the handle of the prick incision lance has an underside which complements the upper side of the handle of the puncturing tube and also has two detent pins and a socket groove for a catheter.

4. The medical puncturing instrument according to claim 3, characterized in that the handle of the prick incision lance has grooves on the upper side.

5. The medical puncturing instrument according to claim 4, wherein:
   said medical puncturing instrument can be divided over its entire length; and
   each half of the divisible puncturing tube supports a complementary section of a handle fitted with a detent groove.

6. The medical puncturing instrument according to claim 1, characterised in that it can be divided over its entire length.

7. The medical puncturing instrument according to claim 3, characterised in that said medical puncturing instrument can be divided over its entire length.

8. A medical puncturing instrument, for puncturing through tissue, comprising:
   a tube having an inside surface;
   a partially cylindrically curved incision lance with a cutting end at one end thereof, said incision lance having an outer surface which conforms to said tube;
   said cutting end of said incision lance comprises an inner surface and a tip;
   said cutting end of said incision lance defines a longitudinal dimension extending along said end portion of said incision lance;
   said inner surface of said end portion of said prick incision lance being disposed generally parallel to said longitudinal dimension of said cutting end of said incision lance;
   said tube having a first end being disposed adjacent to said cutting end of said incision lance;
   said first end of said tube comprises a bent portion being bent with respect to said longitudinal dimension of said end portion of said incision lance, such that said tip portion of said puncturing tube contacts said inner surface of said end portion of said prick incision lance; and
   said first end of said tube has an outer radius, wherein an end of said outer radius adjoins said inner surface of said end portion of said incision lance.

9. The medical puncturing instrument according to claim 8, wherein:
   said tube comprises a major portion having a cylindrical shape;

said major portion of said tube has an inner cylindrical surface;

said inner cylindrical surface of said major portion of said tube has a circumference;

said incision lance conforms to said inner cylindrical surface of said major portion of said tube;

said incision lance is disposed about a limited portion of the circumference of said inner cylindrical surface of said tube;

said tube defines a central longitudinal axis, the central longitudinal axis being centrally disposed with respect to said major portion of said tube;

said bent portion of said first end of said tube is bent inwardly, towards the central longitudinal axis of said tube;

said major portion of said tube is substantially straight with respect to the longitudinal axis of said tube; and said end portion of said incision lance is substantially straight with respect to the longitudinal axis of said tube.

10. The medical puncturing instrument according to claim 9, wherein said tube comprises a second end configured as a tube handle for being held by an operator of the puncturing instrument.

11. The medical puncturing instrument according to claim 10, wherein:

said lance is for fitting inside said tube; and said lance surface which conforms to said tube conforms to said inside surface of said tube.

12. The medical puncturing instrument according to claim 11, comprising:

an instrument handle for being held by the operator of the puncturing instrument; and said lance comprises an end configured as a lance handle for being held by an operator, the underside of said lance handle being configured to conform to said tube handle so that said lance handle and said tube handle can fit together to form said instrument handle.

13. The medical puncturing instrument according to claim 12, wherein;

said lance handle comprises at least one detent pin;

said tube handle comprises at least one detent groove; and said at least one detent pin being for fitting into said at least one detent groove for holding said lance handle and said tube handle together to form said instrument handle.

14. The medical puncturing instrument according to claim 13, wherein said lance handle comprises a socket groove for placing a catheter.

15. The medical puncturing instrument according to claim 14, wherein:

said tube comprises two half tubes, said tube being divided along the entire length of said tube into said two half tubes; and said second end of said tube comprises two half second ends, and each of said two half tubes having one of said two half second ends.

16. The medical puncturing instrument according to claim 15, wherein:

said tube handle comprises two half tube handles; and each of said two half second ends of each of said two half tubes being configured to form said half tube handles.

17. The medical puncturing instrument according to claim 16, wherein said at least one detent groove comprises at least two detent grooves;

each of said two half tube handles comprises at least one of said at least two detent grooves; and said lance handle comprises fluting grooves on the upper side of said lance handle, said fluting grooves for making the puncturing instrument easier to manipulate.

18. A medical puncturing instrument, for puncturing through tissue, comprising:

a tube having an inside surface;

a partially cylindrically curved incision lance with a cutting end at one end thereof, said incision lance having a surface which conforms to said tube;

said tube having a first end for being adjacent to said cutting end of said incision lance, said first end of said tube being bent and being disposed adjacent said cutting end of said incision lance;

said tube comprises a major portion having a cylindrical shape;

said major portion of said tube having an inner cylindrical surface;

said inner cylindrical surface of said major portion of said tube having a circumference;

said incision lance conforming to said inner cylindrical surface of said major portion of said tube;

said incision lance being disposed about a limited portion of the circumference of said inner cylindrical surface of said tube;

said bent portion of said first end of said tube being bent inwardly and across said tube to make contact with said inner surface of said incision lance; and said incision lance being disposed opposite the area of initiation of said bent portion of said first end of said tube.

19. The medical puncturing instrument according to claim 18, wherein:

said tube defines a central longitudinal axis, the central longitudinal axis being centrally disposed with respect to said major portion of said tube;

said major portion of said tube is substantially straight with respect to the longitudinal axis of said tube; and said end portion of said incision lance is substantially straight with respect to the longitudinal axis of said tube.

20. The medical puncturing instrument according to claim 19, wherein:

said tube comprises a second end configured as a tube handle for being held by an operator of the puncturing instrument;

said lance is for fitting inside said tube;

said lance surface which conforms to said tube conforms to said inside surface of said tube;

said medical puncturing instrument further comprises an instrument handle for being held by the operator of the puncturing instrument;

said lance comprises an end configured as a lance handle for being held by an operator, the underside of said lance handle being configured to conform to said tube handle so that said lance handle and said tube handle can fit together to form said instrument handle;

said lance handle comprises at least one detent pin;

said tube handle comprises at least one detent groove;

said at least one detent pin being for fitting into said at least one detent groove for holding said lance handle and said tube handle together to form said instrument handle;

said lance handle comprises a socket groove for placing a catheter;

said tube comprises two half tubes, said tube being divided along the entire length of said tube into said two half tubes;

said second end of said tube comprises two half second ends, and each of said two half tubes having one of said two half second ends;

said tube handle comprises two half tube handles; each of said two half second ends of each of said two half tubes being configured to form said half tube handles;

said at least one detent groove comprises at least two detent grooves;

each of said two half tube handles comprises at least one of said at least two detent grooves; and said lance handle comprises fluting grooves on the upper side of said lance handle, said fluting grooves for making the puncturing instrument easier to manipulate.

* * * * *

UNITED STATES PATENT AND TRADEMARK OFFICE
CERTIFICATE OF CORRECTION

PATENT NO. : 5,403,296
DATED : April 4, 1995
INVENTOR(S) : Klaus Möhring; Josef Magasi It is certified that error appears in the above-indentified patent and that said Letters Patent is hereby corrected as shown below:

Column 1, lines 41-43, delete "When inserting this instrument a high resistance has to be overcome since its point penetrates bluntly into the skin and drives out the tissue." and insert therefor
-- In this device also the circular ring-shaped end edges of the cannula form a punching tool, which has the previously mentioned disadvantages. --

Column 1, line 57, after "bend" insert
-- or pipe elbow --.
Column 1, line 59, change "curved" to -- curve --.
Column 2, line 1, change "not-" to -- not --.
Column 2, line 7, after "itself" delete the comma.
Column 2, line 26, before "in that" delete "achieved".
Column 2, lines 48,49, between lines 48 and 49 insert the following paragraph:
-- In an advantageous manner the opening edge of the pipe bend section of the puncturing tube is cut by a grinding process. The bend is worked upon with a profiled tool, starting from the inner bend portion to the puncturing tube by means of a transverse or plunge grinder in the extension direction of the separation plane of the puncturing tube. A control of the feed motion of the grinding tool can however also be used for the machining. --.

UNITED STATES PATENT AND TRADEMARK OFFICE
CERTIFICATE OF CORRECTION

PATENT NO. : 5,403,296
DATED : April 4, 1995
INVENTOR(S) : Klaus Möhring; Josef Magasi It is certified that error appears in the above-indentified patent and that said Letters Patent is hereby corrected as shown below:

```
Column 2, line 50, change "drawing" to -- drawings --.
Column 3, line 7, after "bend" insert -- or elbow --.
Column 2, line 8, after "bend" insert -- or elbow --.
Column 3, line 40, change "the, manipulation" to
          -- the manipulation --.
Column 4, lines 36,37, delete "said medical puncturing
          instrument" and insert therefor -- it --.
```

Signed and Sealed this

Thirtieth Day of April, 1996

Attest:

BRUCE LEHMAN

*Attesting Officer*     *Commissioner of Patents and Trademarks*